United States Patent
Kanazawa et al.

(10) Patent No.: US 11,880,374 B2
(45) Date of Patent: *Jan. 23, 2024

(54) DOCUMENT SEARCH SUPPORT DEVICE

(71) Applicants: SHIMADZU CORPORATION, Kyoto (JP); OSAKA UNIVERSITY, Suita (JP)

(72) Inventors: Shinji Kanazawa, Kyoto (JP); Satoshi Shimizu, Kyoto (JP); Fumio Matsuda, Suita (JP)

(73) Assignees: Shimadzu Corporation, Kyoto (JP); OSAKA UNIVERSITY, Suita (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/739,847

(22) Filed: May 9, 2022

(65) Prior Publication Data
US 2022/0382767 A1    Dec. 1, 2022

(30) Foreign Application Priority Data
May 28, 2021 (JP) .................. 2021-090190

(51) Int. Cl.
*G06F 16/2457* (2019.01)
*G06F 16/2458* (2019.01)
(Continued)

(52) U.S. Cl.
CPC ...... *G06F 16/24578* (2019.01); *G06F 16/248* (2019.01); *G06F 16/2462* (2019.01); *G06F 16/93* (2019.01)

(58) Field of Classification Search
None
See application file for complete search history.

(56) References Cited

U.S. PATENT DOCUMENTS 11,016,964 B1 * 5/2021 Hinegardner ....... G06F 16/2428
11,386,096 B2 * 7/2022 Malik .................. G06F 16/367
(Continued)

FOREIGN PATENT DOCUMENTS

WO    2020/230704 A1    11/2020

OTHER PUBLICATIONS

Garuda Platform, The Systems Biology Institute, specified non-profit corporation, searched on May 13, 2021, URL: http://www.garuda-alliance.org/about.html.
(Continued)

*Primary Examiner* — Kim T Nguyen
(74) *Attorney, Agent, or Firm* — Muir Patent Law, PLLC

(57) ABSTRACT

A device to support work of searching document data for interpreting an information analysis result of analysis data obtained by analyzing a sample containing an analyte, includes: an acquisition unit to acquire first information for identifying the analyte from the analysis data; a reception unit to receive input of second information for searching data of a document for interpreting the information analysis result of the analysis data; an extraction unit to extract, based on the first and second information, terms relevant to the information analysis result, from among terms in data of documents in a database; a calculation unit to calculate, for each relevant term, relevance scores indicating a relevance degree between the relevant term and the first information, and a relevance degree between the relevant term and the second information; and a processing unit to obtain an index value of statistical likelihood from the relevance scores.

13 Claims, 9 Drawing Sheets

(51) Int. Cl.
*G06F 16/248* (2019.01)
*G06F 16/93* (2019.01)

(56) References Cited

U.S. PATENT DOCUMENTS

| | | | | |
|---|---|---|---|---|
| 11,489,859 | B2* | 11/2022 | Reddy | H04L 63/1433 |
| 11,537,788 | B2* | 12/2022 | Akhondi | G06F 40/20 |
| 11,593,409 | B2* | 2/2023 | Gentilcore | G06F 21/31 |
| 11,630,824 | B2* | 4/2023 | Ishikawa | G06F 16/248 |
| | | | | 707/769 |
| 11,630,829 | B1* | 4/2023 | Thunuguntla | G06F 16/24575 |
| | | | | 707/723 |
| 2019/0278777 | A1* | 9/2019 | Malik | G06F 16/9024 |
| 2019/0364068 | A1* | 11/2019 | Reddy | G06F 16/24578 |
| 2022/0269703 | A1* | 8/2022 | Gentilcore | G06F 16/24578 |
| 2022/0382767 | A1* | 12/2022 | Kanazawa | G06F 16/33 |
| 2023/0086791 | A1* | 3/2023 | Bierner | G06F 16/24575 |
| | | | | 707/722 |
| 2023/0099588 | A1* | 3/2023 | Zhou | G06F 16/9038 |
| | | | | 707/765 |
| 2023/0119590 | A1* | 4/2023 | Bal | G06F 16/322 |
| | | | | 707/754 |
| 2023/0153310 | A1* | 5/2023 | Yun | G06N 20/00 |
| | | | | 707/727 |
| 2023/0153336 | A1* | 5/2023 | Liu | G06F 16/3329 |
| | | | | 707/730 |

OTHER PUBLICATIONS

Pubmed, searched on May 13, 2021, URL:https://www.ncbi.nlm.nih.gov/pubmed.

* cited by examiner

Fig. 7

| order | Score | input term compound | input term user | recommended term | FDR ≤ 0.1 |
|---|---|---|---|---|---|
| 1 | 0.005102041 | Pyruvate Kinase | Breast Neoplasms | Phosphofructokinase-1, Liver Type | TRUE |
| 2 | 0.005102041 | Pyruvate Carboxylase | Breast Neoplasms | Phosphofructokinase-1, Liver Type | TRUE |
| 3 | 0.005102041 | Phosphoenolpyruvate Carboxykinase (ATP) | Breast Neoplasms | Phosphofructokinase-1, Liver Type | TRUE |
| 4 | 0.001986861 | Pyruvate Kinase | Breast Neoplasms | Lactate Dehydrogenase 5 | TRUE |
| 5 | 0.00170785 | Pyruvate Kinase | Breast Neoplasms | Glucose-6-Phosphate Isomerase | TRUE |
| 6 | 0.001419338 | Pyruvate Kinase | Breast Neoplasms | Phosphofructokinases | TRUE |
| 7 | 0.001054002 | Pyruvate Kinase | Breast Neoplasms | Pyrimidine Phosphorylases | TRUE |
| 8 | 0.001031105 | Phosphoenolpyruvate Carboxykinase (ATP) | Breast Neoplasms | Nuclear Receptor Interacting Protein 1 | TRUE |
| 9 | 0.001016731 | Pyruvate Kinase | Breast Neoplasms | Hexokinase | TRUE |
| 10 | 0.00096751 | Pyruvate Kinase | Breast Neoplasms | Phosphofructokinase-2 | TRUE |
| 11 | 0.000955232 | Pyruvate Kinase | Breast Neoplasms | Phosphofructokinase-1 | TRUE |
| 12 | 0.00094948 | Pyruvate Kinase | Breast Neoplasms | Adenofibroma | TRUE |
| 13 | 0.000866363 | Pyruvate Kinase | Breast Neoplasms | Phosphoglycerate Mutase | TRUE |
| 14 | 0.00085034 | Phosphoenolpyruvate | Breast Neoplasms | Tartronates | TRUE |
| ⋮ | | | | | |
| 30 | 0.000436623 | Pyruvate Carboxylase | Breast Neoplasms | Methylmalonyl-CoA Decarboxylase | TRUE |
| 31 | 0.000432526 | Phosphoenolpyruvate Carboxykinase (ATP) | Breast Neoplasms | Nuclear Receptor Subfamily 2, Group C, Member 1 | TRUE |
| 32 | 0.000408951 | Pyruvate Kinase | Breast Neoplasms | Fibroblast Growth Factor 3 | FALSE |
| 33 | 0.000396209 | Pyruvate Kinase | Breast Neoplasms | Fatty Acid Synthases | FALSE |
| 34 | 0.000371535 | Pyruvate Kinase | Breast Neoplasms | Glucosephosphate Dehydrogenase | FALSE |
| 35 | 0.000329658 | Phosphoenolpyruvate Carboxykinase (ATP) | Breast Neoplasms | Hepatocyte Nuclear Factor 3-alpha | FALSE |
| 36 | 0.000328362 | Pyruvate Kinase | Breast Neoplasms | Estradiol Dehydrogenases | FALSE |
| 37 | 0.00029956 | Pyruvate Kinase | Breast Neoplasms | Heterogeneous Nuclear Ribonucleoprotein A1 | FALSE |
| 38 | 0.00028786 | Pyruvate Kinase | Breast Neoplasms | Keratin-19 | FALSE |
| 39 | 0.000283447 | Pyruvate Carboxylase | Breast Neoplasms | Tartronates | FALSE |
| ⋮ | | | | | |
| 55918 | 0 | Phosphoenolpyruvate Carboxykinase (ATP) | Breast Neoplasms | Lissamine Green Dyes | FALSE |
| 55919 | 0 | Pyruvate Carboxylase | Breast Neoplasms | Lissamine Green Dyes | FALSE |
| 55920 | 0 | Pyruvate Kinase | Breast Neoplasms | Atropine Derivatives | FALSE |

Fig. 8

| order | Score | input term compound | input term user | recommended term | FDR ≤ 0.1 |
|---|---|---|---|---|---|
| 1 | 0.005102041 | Pyruvate Kinase | Breast Neoplasms | Phosphofructokinase-1, Liver Type | TRUE |
| 2 | 0.005102041 | Pyruvate Carboxylase | Breast Neoplasms | Phosphofructokinase-1, Liver Type | TRUE |
| 3 | 0.005102041 | Phosphoenolpyruvate Carboxykinase (ATP) | Breast Neoplasms | Phosphofructokinase-1, Liver Type | TRUE |
| 4 | 0.001986861 | Pyruvate Kinase | Breast Neoplasms | Lactate Dehydrogenase 5 | TRUE |
| 5 | 0.00170785 | Pyruvate Kinase | Breast Neoplasms | Glucose-6-Phosphate Isomerase | TRUE |
| 6 | 0.001419338 | Pyruvate Kinase | Breast Neoplasms | Phosphofructokinases | TRUE |
| 7 | 0.001054002 | Pyruvate Kinase | Breast Neoplasms | Pyrimidine Phosphorylases | TRUE |
| 8 | 0.001031105 | Phosphoenolpyruvate Carboxykinase (ATP) | Breast Neoplasms | Nuclear Receptor Interacting Protein 1 | TRUE |
| 9 | 0.001016731 | Pyruvate Kinase | Breast Neoplasms | Hexokinase | TRUE |
| 10 | 0.00096751 | Pyruvate Kinase | Breast Neoplasms | Phosphofructokinase-2 | TRUE |
| 11 | 0.000955232 | Pyruvate Kinase | Breast Neoplasms | Phosphofructokinase-1 | TRUE |
| 12 | 0.00094948 | Pyruvate Kinase | Breast Neoplasms | Adenofibroma | TRUE |
| 13 | 0.000866363 | Pyruvate Kinase | Breast Neoplasms | Phosphoglycerate Mutase | TRUE |
| 14 | 0.00085034 | Phosphoenolpyruvate | Breast Neoplasms | Tartronates | TRUE |
| ⋮ | | | | | |
| 30 | 0.000436623 | Pyruvate Carboxylase | Breast Neoplasms | Methylmalonyl-CoA Decarboxylase | TRUE |
| 31 | 0.000432526 | Phosphoenolpyruvate Carboxykinase (ATP) | Breast Neoplasms | Nuclear Receptor Subfamily 2, Group C, Member 1 | TRUE |
| 32 | 0.000408951 | Pyruvate Kinase | Breast Neoplasms | Fibroblast Growth Factor 3 | FALSE |
| 33 | 0.000396209 | Pyruvate Kinase | Breast Neoplasms | Fatty Acid Synthases | FALSE |
| 34 | 0.000371535 | Pyruvate Kinase | Breast Neoplasms | Glucosephosphate Dehydrogenase | FALSE |
| 35 | 0.000329658 | Phosphoenolpyruvate Carboxykinase (ATP) | Breast Neoplasms | Hepatocyte Nuclear Factor 3-alpha | FALSE |
| 36 | 0.000328362 | Pyruvate Kinase | Breast Neoplasms | Estradiol Dehydrogenases | FALSE |
| 37 | 0.00029956 | Pyruvate Kinase | Breast Neoplasms | Heterogeneous Nuclear Ribonucleoprotein A1 | FALSE |
| 38 | 0.00028786 | Pyruvate Kinase | Breast Neoplasms | Keratin-19 | FALSE |
| 39 | 0.000283447 | Pyruvate Carboxylase | Breast Neoplasms | Tartronates | FALSE |

Fig. 9

| order | Score | input term compound | input term user | recommended term | FDR ≤ 0.1 |
|---|---|---|---|---|---|
| 1 | 0.005102041 | Pyruvate Kinase | Breast Neoplasms | Phosphofructokinase-1, Liver Type | TRUE |
| 2 | 0.005102041 | Pyruvate Carboxylase | Breast Neoplasms | Phosphofructokinase-1, Liver Type | TRUE |
| 3 | 0.005102041 | Phosphoenolpyruvate Carboxykinase (ATP) | Breast Neoplasms | Phosphofructokinase-1, Liver Type | TRUE |
| 4 | 0.001986861 | Pyruvate Kinase | Breast Neoplasms | Lactate Dehydrogenase 5 | TRUE |
| 5 | 0.00170785 | Pyruvate Kinase | Breast Neoplasms | Glucose-6-Phosphate Isomerase | TRUE |
| 6 | 0.001419338 | Pyruvate Kinase | Breast Neoplasms | Phosphofructokinases | TRUE |
| 7 | 0.001054002 | Pyruvate Kinase | Breast Neoplasms | Pyrimidine Phosphorylases | TRUE |
| 8 | 0.001031105 | Phosphoenolpyruvate Carboxykinase (ATP) | Breast Neoplasms | Nuclear Receptor Interacting Protein 1 | TRUE |
| 9 | 0.001016731 | Pyruvate Kinase | Breast Neoplasms | Hexokinase | TRUE |
| 10 | 0.00096751 | Pyruvate Kinase | Breast Neoplasms | Phosphofructokinase-2 | TRUE |
| 11 | 0.000955232 | Pyruvate Kinase | Breast Neoplasms | Phosphofructokinase-1 | TRUE |
| 12 | 0.00094948 | Pyruvate Kinase | Breast Neoplasms | Adenofibroma | TRUE |
| 13 | 0.000866363 | Pyruvate Kinase | Breast Neoplasms | Phosphoglycerate Mutase | TRUE |
| 14 | 0.00085034 | Phosphoenolpyruvate | Breast Neoplasms | Tartronates | TRUE |

Fig. 10

| CATEGORY | NUMBER OF MeSH TERMS FOR FDR ≤ 0.1 | NUMBER OF MeSH TERMS FOR FDR > 0.1 | TOTAL |
|---|---|---|---|
| CANCER | 500 | 200 | 700 |
| INFECTIOUS DISEASE | 800 | 2000 | 2800 |
| TOTAL | 1300 | 2200 | 3500 |

DOCUMENT SEARCH SUPPORT DEVICE

TECHNICAL FIELD

The present invention relates to a document search support device.

BACKGROUND ART

In a living organism, activities of genome and protein change under the environmental influences such as diet, drug, exercise, and various types of stress. Since it is considered that the results under the environmental influences are reflected in various metabolites including low-molecular compounds such as organic acids and amino acids in the living organism, valuable information on biological functions can be obtained by analyzing metabolites in the living organism. A series of techniques for comprehensively detecting metabolites in a living organism and analyzing the results are called metabolomics or metabolome analysis, and are used in a wide range of fields such as engineering fields such as food engineering and metabolic engineering, and agricultural fields, as well as fields of medicine and pharmacy such as diagnosis of diseases, drug discovery, search for biomarkers, and researches on lifestyle and health.

In metabolomics, a comprehensive qualitative analysis or quantitative analysis of metabolites contained in a biological sample such as blood (serum, plasma) and urine is generally performed using a gas chromatograph mass spectrometer (GC/MS) or a liquid chromatograph mass spectrometer (LC/MS) (hereinafter, both are referred to as a chromatograph mass spectrometer). By using a predetermined analysis tool to statistically analyze analysis data obtained by the chromatograph mass spectrometer, it is possible to obtain a list of metabolites changed as a result of drug administration, for example, and a list of metabolites whose content in a living organism increased or decreased in a specific disease patient (Non Patent Literature 1).

When a metabolite list is obtained, the metabolite list is medically and pharmaceutically interpreted, and the relationship between the metabolite and the action mechanism of the drug and the relationship between the metabolite and the pathogenic mechanism of the disease are estimated. In order to interpret the metabolite list, it is necessary to search an appropriate literature from among a large number of literatures containing reports of results of studies performed in the past in the field and necessary to read the literature.

One of representative databases electronically storing information on such literatures is the database MEDLINE run by the US National Library of Medicine (USNLM). Literature information stored in MEDLINE can be searched by using, for example, a search function of PubMed, a search engine provided on the web by the USNLM (see Non Patent Literature 2).

Terms of Medical Subject Heading (MeSH), which is a medical literature thesaurus, are assigned to every literature included in MEDLINE so that search can be efficiently performed. MeSH is set so that medical terms having the same meaning can be searched in a unified manner. For example, literatures including the medical term "cancer", "tumor", or "neoplasm", which all represent "cancer", are given "neoplasms" as a MeSH term. Therefore, by searching "neoplasms" as a keyword, it is possible to extract all medical literatures including terms representing "cancer".

Thus, the literatures included in MEDLINE can be searched in a unified manner by using MeSH terminology. However, the amount of literatures is enormous, and results of studies of the same medical field are sometimes described in some literatures from different viewpoints in segmented and specialized individual fields. In order to correctly search for literatures containing information useful for interpretation of the metabolite list from such amount of literatures, it is necessary for the interpreter to appropriately set search keywords including the MeSH terminology. Such appropriate setting of search keywords depends largely on the knowledge of the interpreter.

On the other hand, an information analyzer is disclosed in Patent Literature 1. The information analyzer first acquires information for identifying an analyte from a result of analyzing measurement data of a biological sample containing the analyte. Then the device extracts, from a database in which document data is stored, terminology related to the analyte on the basis of the acquired information, and presents the terminology to a user. By using, as keywords, the terminology presented by this information analyzer, appropriate literature search can be performed even when the interpreter does not have sufficient knowledge.

CITATION LIST

Patent Literature

Patent Literature 1: WO 2020/230704 A

Non Patent Literature

Non Patent Literature 1: Garuda Platform, The Systems Biology Institute, specified non-profit corporation, [online], [searched on May 13, 2021], Internet Non Patent Literature 2: PubMed, [online], [searched on May 13, 2021], Internet

SUMMARY OF INVENTION

Technical Problem

The information analyzer described above presents all the relevant terms to the user when relevant terms are extracted. When the user searches literatures using, as keywords, all the relevant terms presented, it may be an excessive narrowing and may cause omission in searching. On the other hand, when the user searches literatures using, as a keyword, each of the relevant terms presented one by one, omission in searching can be avoided, but in this case, the number of literatures extracted becomes too large. Therefore, the user should select, as a keyword, appropriate one or a plurality of relevant terms from all the presented relevant terms. When, however, the selected relevant term is not appropriate, it is not possible to extract proper literature useful for interpretation.

Though metabolomics is taken as an example here, there is a similar problem also in interpreting information analysis results of analysis data in lipidomics (lipid analysis), proteomics (protein analysis), genomics (gene analysis), multiomics, which is a comprehensive analysis method, or the like.

A problem to be solved by the present invention is to make it possible to efficiently extract a literature useful for interpretation of a result of analyzing information on analysis data of a sample containing an analyte.

Solution to Problem

A document search support device according to the present invention made to solve the above problems is a device configured to support work of searching document data used for interpretation of an information analysis result of analysis data obtained by analyzing a sample containing an analyte using an analyzer, the document search support device including:

an information acquisition unit configured to acquire first information for identifying the analyte from the analysis data;

an information reception unit configured to receive input of second information for searching data of a document used for interpretation of the information analysis result of the analysis data;

an extraction unit configured to extract, based on the first information and the second information, a plurality of relevant terms which are terms relevant to the information analysis result of the analysis data, from among terms included in data of documents in a database where data of documents is stored;

a score calculation unit configured to calculate, for each of the plurality of relevant terms, a relevance score indicating a degree of relevance between the relevant term and the first information, and a relevance score indicating a degree of relevance between the relevant term and the second information; and a statistical processing unit configured to obtain an index value of statistical likelihood of each of the plurality of relevant terms from the relevance scores of the relevant term.

Advantageous Effects of Invention

According to the present invention, an index value of statistical likelihood is obtained from relevance scores for each of a plurality of extracted relevant terms. The "index value of statistical likelihood" of a relevant term in the present invention is a value representing the probability that the relevant term has been extracted (not) by chance. Therefore, the user can, referring to the index value of likelihood of each relevant term, determine which relevant term to use as a keyword, and it is possible to efficiently search for literatures useful for interpretation of information analysis results by using the relevant term.

BRIEF DESCRIPTION OF DRAWINGS

FIG. 7 is a diagram illustrating an example of a processing result displayed on a display unit.

FIG. 8 is a diagram illustrating another example of the processing result displayed on the display unit.

FIG. 9 is a diagram illustrating still another example of the processing result displayed on the display unit.

FIG. 10 is an example of a cross-tabulation table created by categorizing MeSH terms.

DESCRIPTION OF EMBODIMENTS

[Outline of Information Provision System]

Figure 1:
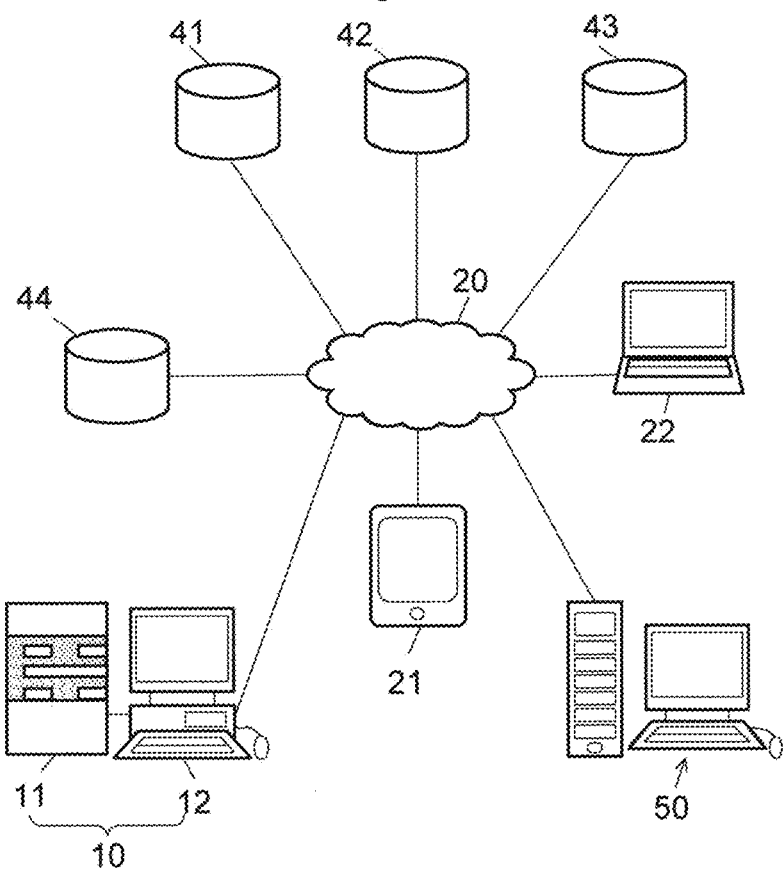
FIG. 1 is a schematic diagram of an information provision system including a document search support device according to an embodiment of the present invention.

An embodiment of the present invention will be described below with reference to the drawings. FIG. 1 is a schematic diagram of an information provision system including a document search support device 50 according to this embodiment.

The information provision system includes an analyzer 10, a plurality of terminal devices (here, a tablet terminal 21 and a personal computer 22 are illustrated), and a plurality of databases 41, 42, 43, and 44 in addition to the document search support device 50. Document data is stored in each of the plurality of databases 41, 42, 43, and 44.

The analyzer 10 includes a device main body 11 that performs analysis by a mechanical operation on a sample containing an analyte, and a personal computer 12 installed with control software for controlling the operation of the device main body 11, processing software for processing data obtained by the device main body 11 performing analysis, and the like. In this present embodiment, a signal value output from a detector included in the device main body 11 as a result of analysis performed by the device main body 11 is referred to as "raw data", and data obtained as a result of processing the raw data by processing software is referred to as "analysis data". A storage device of the personal computer 12 stores raw data and analysis data.

As the analyzer 10, a chromatograph such as liquid chromatography (LC) and gas chromatography (GC), and a chromatograph mass spectrometer such as LC/MS and GC/MS where a mass spectrometer is combined with a chromatograph can be used. When the analyzer 10 is a chromatograph mass spectrometer, graphs such as a chromatogram and a mass spectrum are acquired as analysis data. Coordinate data (e.g., numerical data that is a set of retention time and signal intensity, a set of mass-to-charge ratio m/z value and signal intensity, or the like) representing each point on the graph may be used as the analysis data. Analysis data of any form may be used as long as the type and amount of the analyte contained in the sample can be identified by analyzing the analysis data. In addition, samples to be supplied to the analyzer 10 include liquid samples, gas samples, and solid samples. Liquid samples include urine and blood of animals including humans, and biological samples such as rough extracts obtained by breaking down cellular structures of organisms. In a case where the sample is a biological sample, the analyte is a metabolite, protein, lipid, and the like.

The entity of the document search support device 50 is a computer such as a personal computer or a workstation. The document search support device 50 is a device that supports a user work of searching at least one of the databases 41, 42, 43, and 44 for document data used for interpretation of an information analysis result of the analysis data. A detailed configuration of the document search support device 50 will be described later.

The personal computer 12 of the analyzer 10, the terminal devices 21 and 22, and the document search support device 50 are connected to the databases 41, 42, 43, and 44 via an Internet 20, and can bidirectionally communicate with one another. The personal computer 12 of the analyzer 10, the terminal devices 21 and 22, and the document search support device 50 can use the document data stored in the databases 41, 42, 43, and 44 via the Internet 20.

As the databases 41, 42, 43, and 44, various databases are used according to the type of the sample to be analyzed by the analyzer 10, the type of the analyte contained in the sample, the purpose of analyzing the sample using the analyzer 10, and the like. For example, databases used for interpretation of results of analyzing analysis data of biological samples include gene databases, protein information databases, pharmaceutical information databases, and medical literature databases. Medical literature databases include a medical literature database MEDLINE run by the National Library of Medicine (NLM) of the U.S. The document data stored in the database includes papers, books, dictionaries, and pharmaceutical package inserts.

[Configuration of Document Search Support Device]

Figure 2:
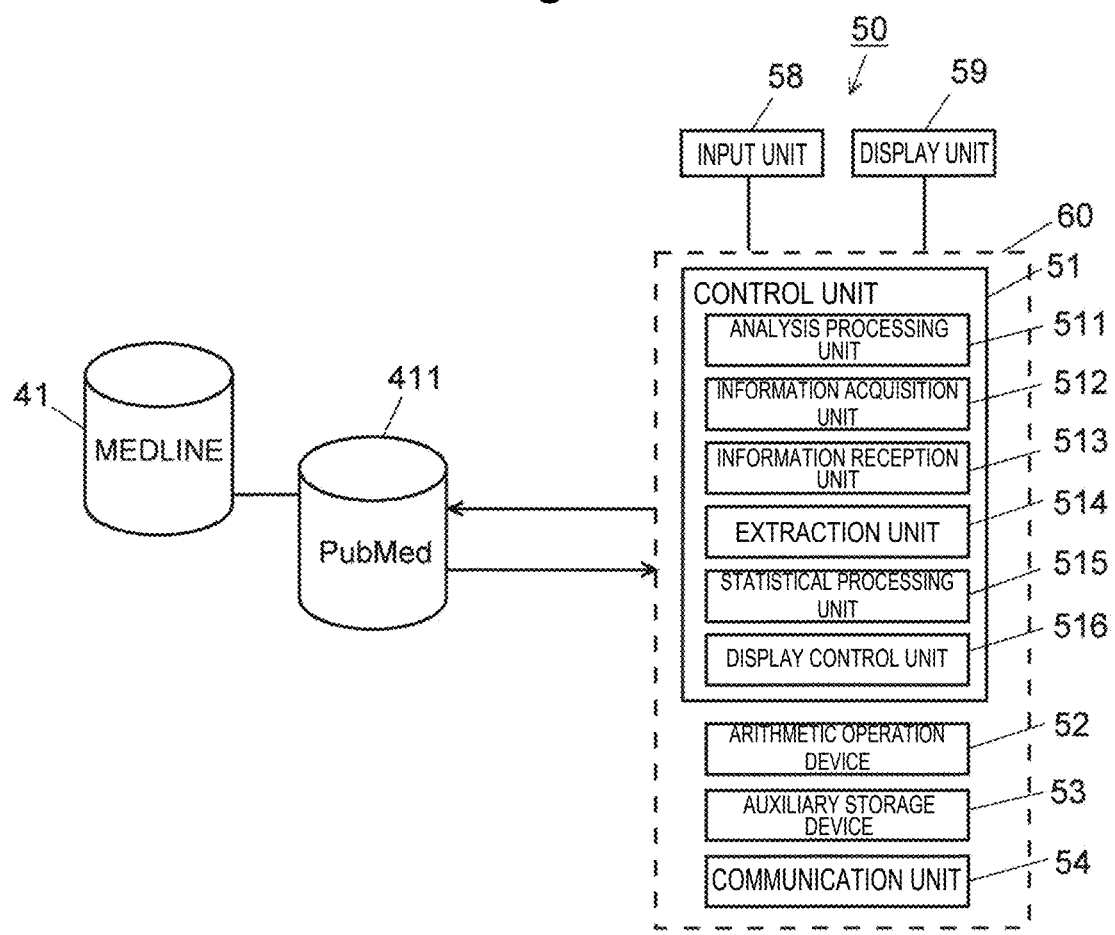
FIG. 2 is a block diagram illustrating a schematic configuration of the document search support device.

FIG. 2 is a block diagram illustrating a schematic configuration of the document search support device 50.

The document search support device 50 includes a device main body 60, and an input unit 58 and a display unit 59 that are connected to this device main body 60. The device main body 60 includes a control unit 51, an arithmetic operation device 52 such as a CPU that executes various arithmetic processing, an auxiliary storage device 53 that stores raw data, analysis data, and the like sent from the personal computer 12 of the analyzer 10 via the Internet 20, and a communication unit 54 that transmits and receives data to and from the database 41 via the Internet 20. FIG. 2 illustrates a state in which the device main body 60 and one database 41 are connected, but a plurality of databases may be connected. In addition, FIG. 2 illustrates a state in which MEDLINE, which is run by the National Library of Medicine (NLM) of the U.S., as the database 41 is connected via PubMed 411. Literatures included in MEDLINE can be searched by using the search function of PubMed 411.

MEDLINE electronically includes a large number of literatures, each of which is given a MeSH term and MeSHID, which are medical literature thesaurus. The large number of MeSH terms given to the literatures included in MEDLINE have a hierarchical structure classified by category, and MeSH terms representing a plurality of subordinate concepts are arranged in a branched state below a MeSH term representing a certain superordinate concept. MeSH terms representing "esophagus disease", "gastrointestinal disease", and the like are arranged below a MeSH term representing "digestive disease" that is a superordinate concept, for example, and MeSH terms representing "gastric ulcer", "duodenal ulcer", "stomach cancer", and the like are arranged below "gastrointestinal disease". MeSHID is given to a MeSH term according to the category of the MeSH term.

The control unit 51 controls operations of the arithmetic operation device 52, the auxiliary storage device 53, and the communication unit 54. In addition, the control unit 51 includes an analysis processing unit 511, an information acquisition unit 512, an information reception unit 513, an extraction unit 514, a statistical processing unit 515, and a display control unit 516 as a functional block. In the present embodiment, the analysis processing unit 511 and the information acquisition unit 512 correspond to the first information acquisition unit of the present invention. The information reception unit 513, the extraction unit 514, and the statistical processing unit 515 correspond to the second information reception unit, the extraction unit, and the statistical processing unit, respectively, of the present invention.

As described above, the entity of the document search support device 50 is a computer, and each function of the control unit 51 is embodied by executing, on the computer, dedicated software installed in advance in the computer. The input unit 58 is a keyboard or a pointing device (mouse or the like) attached to the computer. The display unit 59 is a display monitor of the computer. The auxiliary storage device 53 is a hard disk drive (HDD), a solid state drive (SSD), or the like. The arithmetic operation device 52, the auxiliary storage device 53, and the communication unit 54 are connected with the control unit 51 by an internal bus.

[Processing in Document Search Support Device]

Figure 3:
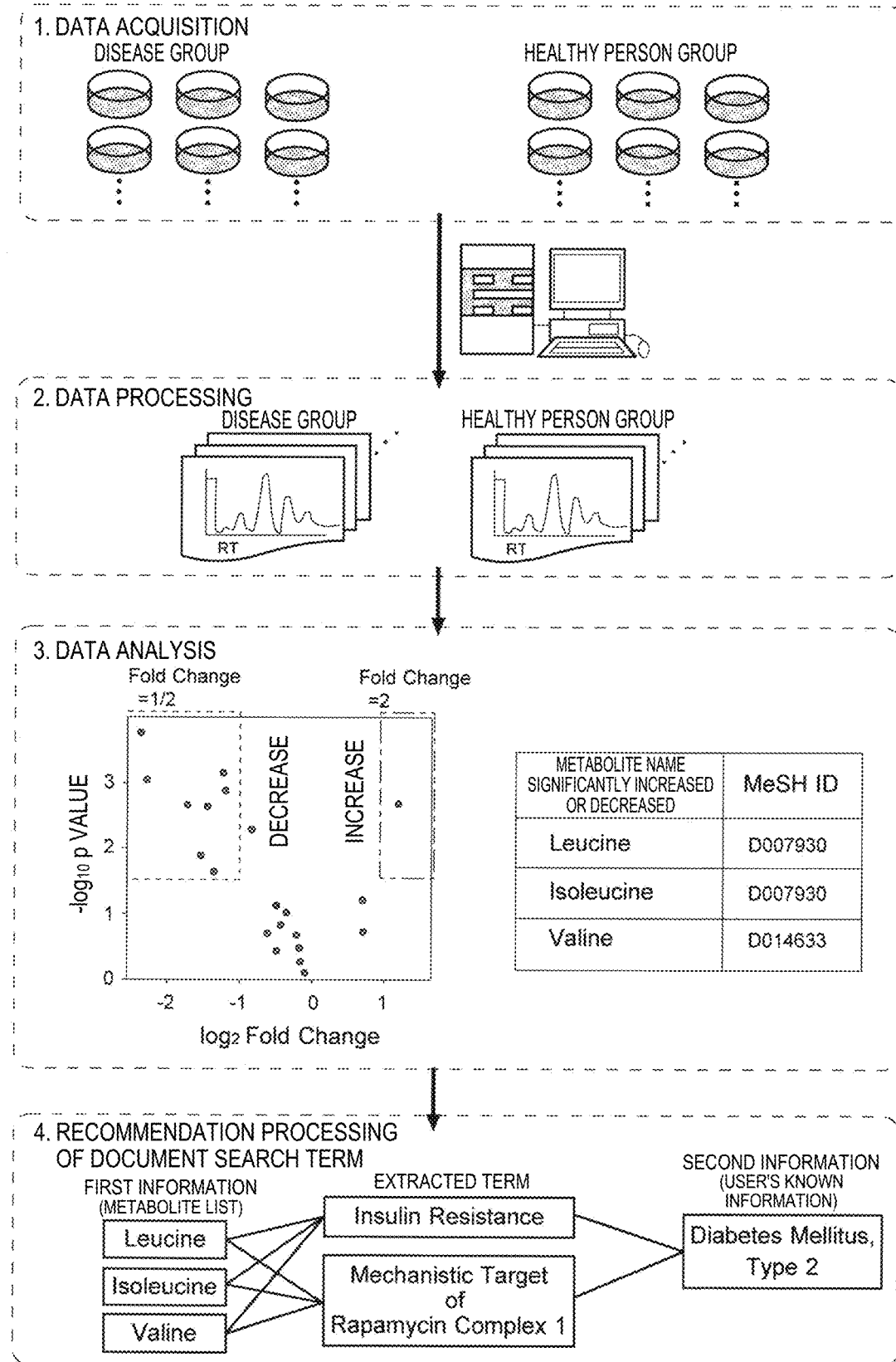
FIG. 3 is an explanatory diagram illustrating an example of processing of extracting a literature search term from analysis data.

Next, processing performed by the document search support device 50 will be described with reference to FIG. 3. FIG. 3 illustrates, as an example, a flow of processing in a case where the analyzer 10 (LC/MS) analyzes samples obtained by performing predetermined pretreatment on blood collected from a plurality of patients (disease group) diagnosed as having type 2 diabetes and blood collected from a plurality of healthy persons (healthy person group).

<1. Data Acquisition>

First, the device main body 11 of the analyzer 10 analyzes samples of the disease group and the healthy person group, acquire raw data.

<2. Data Processing>

Next, the personal computer 12 of the analyzer 10 processes the raw data and obtains analysis data. FIG. 3 illustrates a chromatogram as analysis data, but the analysis data may be a mass spectrum, numerical data including a set of retention time and signal intensity, or numerical data including a set of m/z value and signal intensity. In addition, the analysis data may be a graph presenting a temporal change in the content for each metabolite contained in the sample.

<3. Data Analysis>

Subsequently, the analysis data is sent from the analyzer 10 to the document search support device 50 and stored in the auxiliary storage device 53. In addition, the analysis processing unit 511 analyzes the analysis data stored in the auxiliary storage device 53, and creates data (analysis data) in a form by which metabolites contained in the sample can be identified. Therefore, the analysis processing unit 511 stores in advance an analysis tool necessary for creating analysis data.

Here, it is assumed that the contents of metabolites in the samples of the disease group and the healthy person group are compared by a volcano plot, and a list of metabolites whose contents have significantly varied is created. The volcano plot and the metabolite list correspond to the analysis data. The metabolite list describes the names of metabolites whose contents have significantly varied between the disease group and the healthy person group, and MeSHIDs of the metabolites. MeSHID is attached to a MeSH term according to the category of the MeSH term, and can be acquired from PubMed. In addition, an ID conversion tool (not illustrated) for converting the name of a metabolite into MeSHID may be installed in advance into the document search support device 50, and the analysis processing unit 511 may convert the name of the metabolite described in the metabolite list into MeSHID using the ID conversion tool.

Note that an example in which the analysis data is analyzed using the volcano plot has been described here, multivariate analysis can be used other than this. In addition, the analysis data may be processed by a mapping tool that creates a metabolic map in which metabolic pathways are schematized. In this case, the metabolic map is the analysis data.

In addition, in the present embodiment, the description will be given assuming that the document search support device 50 has a function of analyzing analysis data, but the analyzer 10 may have a function of analyzing analysis data. In addition, any of the terminal devices 21 and 22 may acquire analysis data from the analyzer 10 and analyze the analysis data.

<4. Recommendation Processing of Document Search Term>

When the metabolite list is created, recommendation processing of the document search term is executed. Hereinafter, an example of the recommendation processing will be described.

First Example

Figure 4:
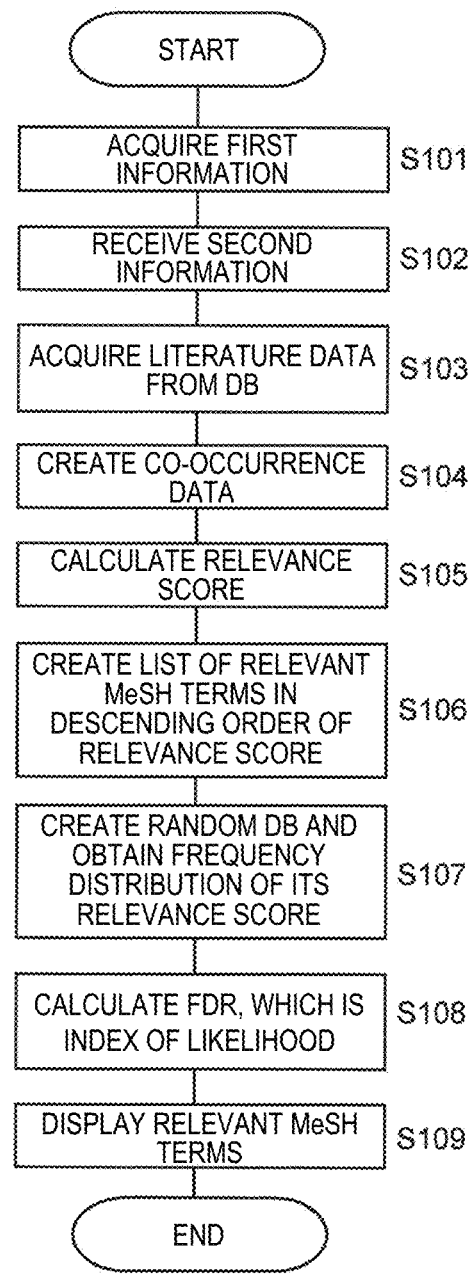
FIG. 4 is a flowchart illustrating an example of extraction processing of document search term.

FIG. 4 is a flowchart illustrating a procedure of recommendation processing of the first example.

In this first example, first, the information acquisition unit 512 extracts a metabolite name described in the metabolite list (step 101). FIG. 3 presents leucine, isoleucine, and valine as metabolite names extracted from the metabolite list. In a case where MEDLINE is used as a database in which document data is stored, the information acquisition unit 512 inquires of PubMED and acquires a MeSH term and a MeSHID corresponding to the metabolite name acquired from the metabolite list. The metabolite name acquired by the information acquisition unit 512 or the MeSH term and the MeSHID corresponding to the metabolite correspond to the first information of the present invention.

Subsequently, the control unit 51 causes the display control unit 516 to display, on the display unit 59, a message prompting the user to input the second information via the input unit 58. Then, when the user inputs the second information using the input unit 58, this second information is received by the information reception unit 513 (step 102). The second information is input by the user as information necessary for searching document data used for interpretation of the result of analysis of analysis data, and is information known by the user. Examples of the second information include terms representing a drug, a disease, a biological species, an organ, an organ, a race, and the like selected in consideration of the purpose of analyzing the analyte contained in the sample, the type of the sample, and the like.

When MEDLINE is used as the database in which the document data is stored, the second information received by the information reception unit 513 is a MeSH term or a MeSHID. In this case, if the term having been input via the input unit 58 is a MeSH term or a MeSHID, the term is received as is by the information reception unit 513. On the other hand, if the term having been input via the input unit 58 is neither a MeSH term nor a MeSHID, the information reception unit 513 inquires of PubMED to acquire the MeSH term or/and the MeSHID corresponding to the input term. FIG. 3 illustrates an example in which (the MeSH term or/and MeSHID of) type 2 diabetes (diabetes mellitus, type 2) is received as the second information.

Next, the extraction unit 514 acquires co-occurrence data, which is information relevant to the first information and the second information, from the document data stored in the database 41. Specifically, the control unit 51 requests PubMed for transmission of data via the Internet 20 via the communication unit 54 (step 103).

Upon receiving the transmission request from the document search support device 50, PubMed obtains literature data stored in MEDLINE from MEDLINE Co-Occurrence (MRCOC) (https://ii.nlm.nih.gov/MRCOC.shtml, [searched on May 12, 2021]), which is one of the services available via PubMed, and transmits the literature data to the document search support device 50. The control unit 51 having received the literature data stores the literature data into the auxiliary storage device 53. The extraction unit 514 reads the literature data stored in the auxiliary storage device 53, and creates co-occurrence data common to MeSHIDs (first MeSHID) of all metabolites included in the metabolite list and MeSHIDs (second MeSHID) of the second information having been input by the user (step 104). The co-occurrence data includes a text file (CoOccurs.txt) in which, in the literature included in the literature data, MeSH terms appearing simultaneously with MeSH terms (first MeSH terms) corresponding to the first MeSHIDs and MeSH terms (second MeSH terms) corresponding to the second MeSHIDs and their MeSHIDs, as well as the value of the co-occurrence frequency are described in association with one another. MeSH terms included in the co-occurrence data correspond to the relevant terms of the present invention. Hereinafter, the MeSH terms included in the co-occurrence data are referred to relevant MeSH terms. FIG. 3 illustrates an example in which the MeSH terms included in co-occurrence data are "Insulin Resistance (D007333)" and "Mechanistic Target of Rapamycin Complex 1 (D000076222)".

When the extraction unit 514 creates co-occurrence data, the statistical processing unit 515 performs an association analysis between each relevant MeSH term included in the co-occurrence data and the first MeSH term and between each relevant MeSH term included in the co-occurrence data and the second MeSH term, thereby obtaining a relevance score representing the level of relevance between the relevant MeSH term and the first MeSH term and the second MeSH term (step 105). Here, for each relevant MeSH term, Confidence value between the relevant MeSH term and the first MeSH term and Confidence value between the relevant MeSH term and the second MeSH term are obtained by calculation, and a product thereof is defined as a relevance score. When relevance scores are obtained for all the relevant MeSH terms, a list of relevant MeSH terms in descending order of relevance score is created (step 106). Therefore, in this example, the extraction unit 514 and PubMed constitute the extraction unit of the present invention. In addition, the statistical processing unit 515 functions as the score calculation unit of the present invention.

The Confidence value is a conditional probability, and depending on selection of the denominator, there are two types of conditional probabilities, a conditional probability from the relevant MeSH term to the first or second MeSH term, and a conditional probability from the first or second MeSH term to the relevant MeSH term. Here, the conditional probability from the relevant MeSH term to the first MeSH term or the second MeSH term is Confidence value. That is, where the number of literatures given the first MeSH term is $[C_1]$, the number of literatures in which the relevant MeSH term and the first MeSH term co-occur is $[C_{1X}]$, the number of literatures given the second MeSH term is $[C_2]$, and the number of literatures in which the relevant MeSH term and the second MeSH term co-occur is $[C_{2X}]$, Confidence values of the first MeSH term and the second MeSH term and the relevance score of the relevant MeSH term are expressed by the following expressions, respectively.

Confidence Value=$[C_{1X}]/[C_1],[C_{2X}]/[C_2]$

Relevance Score=$([C_{1X}]/[C_1])\times([C_{2X}]/[C_2])$

Note that, in this embodiment, the relevance score is obtained by using Confidence value. However, for each relevant MeSH term, Cosine coefficient, Dice coefficient, Simpson coefficient, and Lift value between each relevant MeSH term and the first MeSH term and between each relevant MeSH term and the second MeSH term may be obtained, and the product of these values may be used as the relevance score. Cosine coefficient, Dice coefficient, Simpson coefficient, and Lift value are defined by the following expressions.

Cosine Coefficient=$[C_{1X}]/\sqrt{([C_1]\times[X])},[C_{2X}]/\sqrt{([C_2]\times[X])}$ Dice Coefficient=$[C_{1X}]/\{([C_1]+[X])/2\},[C_{2X}]/\{([C_2]+[X])/2\}$ Simpson Coefficient=$[C_{1X}]/\min([C_1],[X]),[C_{2X}]/\min([C_2],[X])$ Lift Value=Confidence value/($[X]$/Total number of literatures)

In the above expressions, $[X]$ represents the number of literatures given the relevant MeSH term, and min ($[C_1]$, $[X]$) represents the lesser number of $[C_1]$ and $[X]$.

Subsequently, the statistical processing unit 515 performs a test of the statistical superiority of the relevance score of each relevant MeSH term. Specifically, the statistical processing unit 515 obtains all the literatures stored in MEDLINE from MRCOC and creates a random database (DB), and extracts co-occurrence terms that appear simultaneously with the first MeSH term and the second MeSH term from the literatures included in this random DB. Then, the statistical processing unit 515 performs association analyses between each co-occurrence term and the first MeSH term and between each co-occurrence term and the second MeSH term in the same manner as in step 105 described above, calculates the relevance score of each co-occurrence term from Confidence values between each co-occurrence term and the first MeSH term and between each co-occurrence term and the second MeSH term, and obtains a frequency distribution thereof (step 107).

In addition, from the position of the relevance score of each relevant MeSH term in the frequency distribution of the relevance scores of the co-occurring terms extracted from the random DB, the statistical processing unit 515 calculates a false discovery rate (FDR) of each relevant MeSH term, and determines whether or not the FDR of each relevant MeSH term falls within a predetermined range (step 108). That is, in the present example, the statistical processing unit 515 functions as the determination unit of the present invention.

A creation method for the random DB will be described with reference to FIGS. 5A to 5C.

Figure 5A:
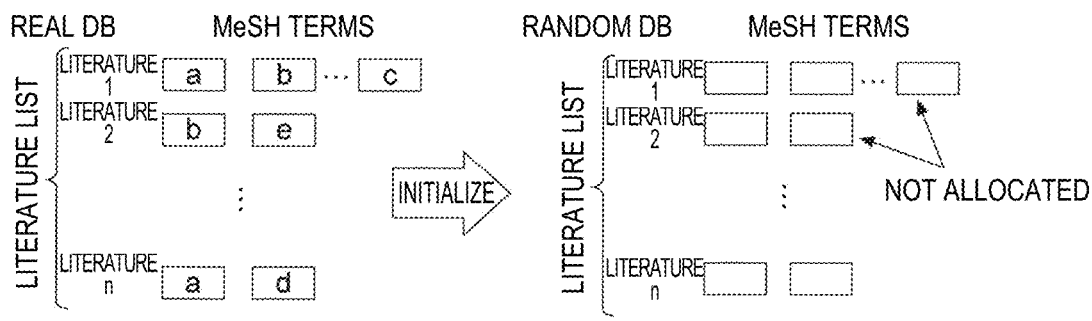
FIGS. 5A to 5C are explanatory diagrams of a creation procedure of a random database.
Figure 5B:
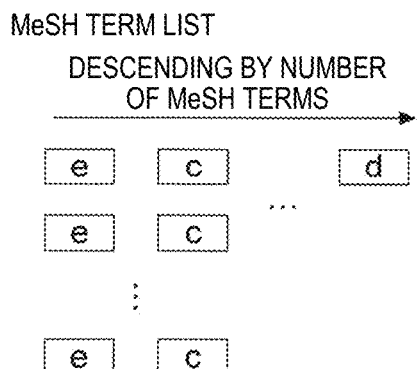
Figure 5C:
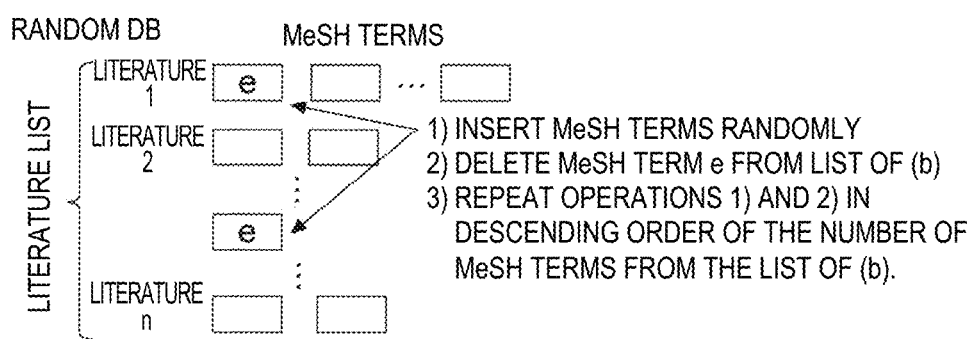

In FIG. 5A, the real database (DB) is a list of literatures stored in MEDLINE and a list of MeSH terms given to all the literatures. FIG. 5A illustrates an example in which Literature 1 is given MeSH terms a, b . . . , c, Literature 2 is given MeSH terms d and e, and Literature n is given MeSH terms a and b.

For such real DB, a DB is created in which MeSH terms are randomly shuffled so that the number of literatures, the number of MeSH terms given to each literature, and the number of appearances of each MeSH term in all literatures become the same those in the real DB. This is the random DB. Specifically, the random DB is created by the following procedure.

(1) MeSH terms given to each literature in the literature list in the real DB are initialized. Due to this, a literature list (initialization literature list) in which a MeSH term is allocated to none of the literatures is created (right side in FIG. 5A).

(2) A list of all MeSH terms given in literatures in the real DB is created. In this list, MeSH terms are arranged in descending order of the number of appearances in the real DB (sorted in descending order) (FIG. 5B).

(3) Assuming that a MeSH term at the top of the list of MeSH terms is X, and the number of its appearances in the real DB is A, A literatures are randomly selected from the initialization literature list, and the MeSH term is allocated to each of the A literatures. In the example of FIG. 5B, the MeSH term X corresponds to the MeSH term e.

(4) Note that, in a case where the number of literatures in the initialization literature list is equal to or less than A, all the literatures in the list are selected, and MeSH terms having no allocation destination are discarded. In addition, in a case where the MeSH term X is allocated to a literature in which the number of allocations of the MeSH terms in the real DB is 1, the literature is excluded from the allocation target of the MeSH terms in the next and subsequent times.

(5) The MeSH term X is deleted from the MeSH term list, as many literatures as the number of appearances B of the MeSH term Y in the real DB are randomly selected from the initialization literature list, for the next MeSH term Y, in the same manner as the processing (3) and (4) performed on the top MeSH term X, and the MeSH term Y is allocated to the literature. In addition, the literature to which as many MeSH terms X as the number of allocations of a MeSH term in the real DB are allocated is excluded from the allocation target of the MeSH terms in the next and subsequent times.

(6) The processing of (5) is continued until there are no more MeSH terms in the MeSH term list.

Figure 6A:
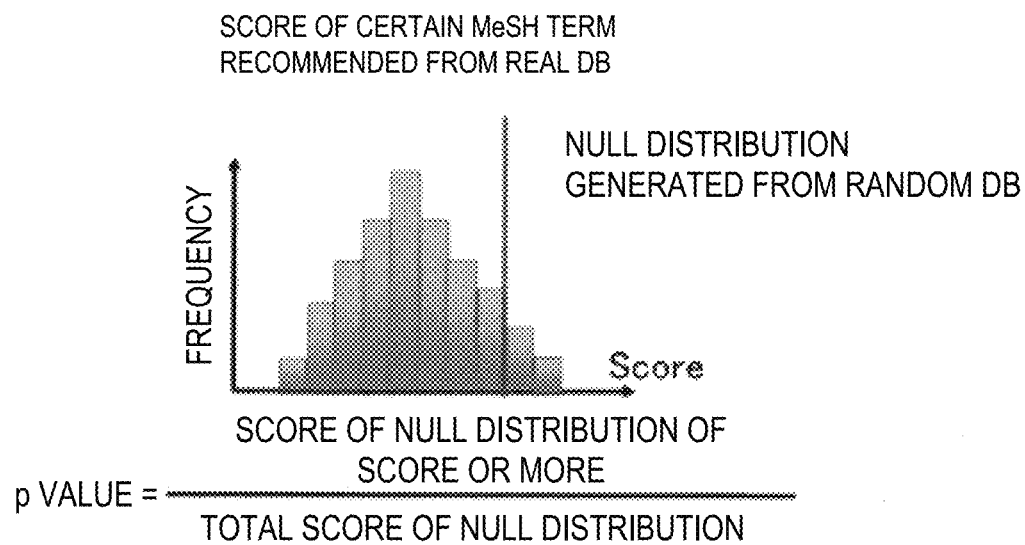
FIGS. 6A and 6B are explanatory diagrams of a p value and a q value of a relevant MeSH term extracted from a real database, where distribution of a relevance score in a random database is calculated as a null distribution.

Targeting the random DB created by the above procedure, a co-occurrence term is extracted in the same manner as the processing performed for the real DB, and its relevance score is obtained. Then, a frequency distribution of the relevance score of the extracted co-occurrence term is generated, and, using this as the null distribution, a p value of the relevant MeSH term extracted from the real DB is obtained by calculation (FIG. 6A). When the value of the relevance score for a relevant MeSH term is S, the p value of the relevant MeSH term is expressed by the following expression.

$p$ value=(score for which the relevance score is $S$ or more in the null distribution)/(total score of the null distribution)

Figure 6B:
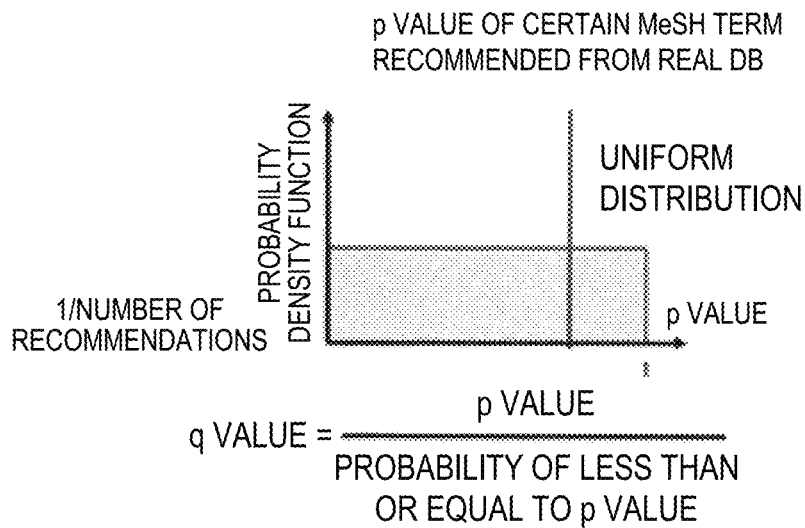

Next, the p value was corrected using Benjamini & Hochberg method (BH method). The BH method is a method for adjusting a false discovery rate (FDR). The FDR is a value obtained by dividing the number of times the true null hypothesis is erroneously rejected (a error) by the total number of times the null hypothesis is rejected, and in the BH method, a q value obtained in the following procedure corresponds to FDR. First, on an assumption that all p values follow a uniform distribution, a frequency distribution thereof is created (FIG. 6B). Then, a value (q value) is calculated by dividing the p value by a probability (area of uniform distribution of p value or less in the graph illustrated in FIG. 6B) that the p value is equal to or less than the p value. The threshold of the q value (FDR) only needs to be a statistically significant value, and in statistical analysis, q value=0.05 or 0.1 is generally selected as the threshold.

When FDR of each relevant MeSH term is obtained, the display control unit 516 creates a table in which the relevant MeSH terms are arranged in descending order of the relevance score together with the relevance score and the determination result of FDR, and displays the table on the display unit 59 (step 109). FIG. 7 illustrates an example of a table to be displayed on the display unit 59 when 55920 relevant MeSH terms have been extracted. In this table, "Score" represents the relevance score and "recommended term" represents the relevant MeSH term. In addition, "input term compound" and "input term user" represent the first and second MeSH terms used for extraction of the relevant MeSH terms. In addition, in this table, as a determination result of FDR, the relevant MeSH terms with FDR≤0.1 are given display "TRUE", and the relevant MeSH terms with FDR>0.1 are given display "FALSE".

The relevant MeSH terms with FDR≤0.1 indicate that they are statistically evaluated as not having been extracted by chance. That is, it is indicated that a relevant MeSH term given "TRUE" is a term with a high possibility that a literature useful for interpretation of an information analysis result of analysis data can be extracted by searching the literature stored in MEDLINE when used as a keyword together with the first MeSH term and the second MeSH term. Therefore, by seeing the determination result of FDR described in the table displayed on the display unit 59, the user can select the relevant MeSH terms to use as keywords for literature search, and use them as keywords for literature search in descending order of relevant MeSH terms having larger relevance scores.

FIG. 7 illustrates an example in which a table where all the extracted relevant MeSH terms are arranged in descending order of the relevance score is displayed on the display unit 59, but the present invention is not limited thereto. FIG. 8 illustrates an example in which in a table where all the extracted relevant MeSH terms are arranged in descending order of the relevance score, the relevant MeSH terms with FDRs falling within a predetermined range (FDR≤0.1) are shaded and given a thick frame such that they are visually distinguishable from the other relevant MeSH terms. In this example, since the region corresponding to the relevant MeSH terms whose FDRs fall within the predetermined range is given the thick frame and the numbers of the relevant MeSH terms are shaded, the user can easily find the relevant MeSH terms that serve as keywords useful for literature search from the table displayed on the display unit 59.

In addition, FIG. 9 illustrates an example in which a table where only relevant MeSH terms whose FDRs fall within a predetermined range (FDR≤0.1) are arranged in descending order of the relevance score is displayed on the display unit 59. In this example, the user is only required to perform literature search using the relevant MeSH terms displayed on the display unit 59.

Example 2

This example is different from the first example in processing of obtaining an index value of statistical likelihood of each relevant MeSH term from the relevance score of the term. Other processing is the same as that in the first example, and thus description thereof is omitted.

First, the statistical processing unit 515 classifies all the extracted relevant MeSH terms (all the relevant MeSH terms presented in the table of FIG. 7 in the example of the first example) into categories, and creates a cross-tabulation table. This cross-tabulation table is a table in which the number of relevant MeSH terms whose FDR is 0.1 or less (the number of giving of "TRUE" in FIG. 7) and the number of relevant MeSH terms whose FDR is greater than 0.1 (the number of giving of "FALSE" in FIG. 7) are summed for each category. For example, FIG. 10 illustrates that when 700 relevant MeSH terms belonging to the category "cancer" are extracted, 500 of the 700 have FDR of 0.1 or less and 200 of the 700 have FDR of greater than 0.1, and illustrates that when 2800 relevant MeSH terms belonging to the category "infectious disease" are extracted, 800 of the 2800 have FDR of 0.1 or less and 2000 of the 2800 have FDR of greater than 0.1.

Next, a chi-square test is performed on the created cross-tabulation table. Specifically, from the total number of relevant MeSH terms for "FDR≤0.1" and the total number of relevant MeSH terms for "FDR>0.1" in the cross-tabulation table, an expected value of the number of the relevant MeSH terms for "FDR≤0.1" and an expected value of the number of the relevant MeSH terms for "FDR>0.1" in each category are obtained by calculation. Then, a test is performed on an assumption that the chi-square value obtained by the following expression that can be calculated from those expected values and the actually aggregated value approximately follows a chi-square distribution.

$$x^2 = \Sigma\{(\text{Actual number} - \text{Expected value})^2/\text{Expected value}\} \quad \text{[Expression 1]}$$

When the chi-square value is larger than a predetermined threshold, it is indicated that there is a difference in ratio of relevant MeSH term of "FDR≤0.1" between the categories, and thus the display control unit 516 displays the category group having the larger ratio of the relevant MeSH term of "FDR≤0.1" on the display unit 59 as the category group useful for search of document data used for interpretation of the information analysis result of analysis data.

Note that FIG. 10 illustrates an example of a case where the extracted relevant MeSH terms are classified into two categories, but naturally the number of categories can be 3 or more. With the chi-squared test, it can be tested whether or not there is a difference in ratio of relevant MeSH term for "FDR≤0.1" between categories in cross tabulation, but it cannot be tested as to which category the ratio of relevant MeSH term of "FDR≤0.1" is significantly higher in. Therefore, it is preferable to perform residual analysis when the number of categories is three or more. In the residual analysis of the present example, the difference between the above-described expected value and the number of actually extracted MeSH terms is defined as the residual. The residual can be regarded as the p value with respect to the normal distribution by standardization and correction. Therefore, it is possible to examine the significance for each category by performing residual analysis for all categories. In this case, since the test is performed by the number of categories, it is preferable to correct the residual using a multiple test correction method such as Benjamini & Hochberg method.

The residual analysis yields a category group that has a significantly higher ratio of the relevant MeSH terms for "FDR≤0.1" to the number of the extracted relevant MeSH terms. Since it is considered that such a category group includes many relevant MeSH terms that can be useful keywords for search of document data used for interpretation of the information analysis result of analysis data, the display control unit 516 displays the category group on the display unit 59 in a form visually distinguished from other category groups.

Note that in the cross-tabulation table presented in FIG. 10, if a certain relevant MeSH term belongs both to the category of "cancer" and the category of "infectious disease", the total number is obtained using it as one relevant MeSH term, but the actual number of the plurality of extracted relevant MeSH terms may be used as the total number. In this case, the total value at the lowermost of the cross-tabulation table presented in FIG. 10 is smaller than the total value of the number of relevant MeSH terms belonging to each category of "cancer" and "infectious disease", but there is no problem in statistical processing.

[Modifications]

In the above embodiment, the document search support device 50 is configured by one personal computer, but some functional blocks of the document search support device 50 may be mounted on a terminal device such as another personal computer or a tablet terminal connected to the document search support device 50 via a communication line. In addition, software that is the entity of each functional block of the document search support device 50 may be stored in an application server connected to the document search support device 50 via a communication line, and the software may be downloaded from the application server to the document search support device 50 as necessary.

In the above examples, the second information is input to the document search support device 50 by the operation on the input unit 58 by the user and is acquired by the information reception unit 513, but the second information may be input to the document search support device 50 from a terminal device connected via the Internet 20.

In the above embodiment, MRCOC, provided on PubMed, is used for acquisition of co-occurrence data, but the document search support device 50 may have a function of generating co-occurrence data. By adopting a co-occurrence index (e.g., Dice coefficient, Jaccard coefficient, Simpson coefficient, Confidence, and the like) suitable for each database of document data to generate co-occurrence data, it is possible to improve usefulness of relevant terms as search narrowing candidates.

In the above embodiment, PubMed is used as the database of document data, but for example, another database such as a literature information provision service or the like operated by a publishing company or the like may be used. In this case, in preprocessing, the content of the biological sample in the analysis data is identifying by the keyword and ID according to the thesaurus used to classify the literatures in the database. In addition, not only an existing database that can be used via the Internet but also an independently constructed database may be used via an arbitrary communication line.

In the above embodiment, the result of the processing by the statistical processing unit 515 is displayed on the display unit 59, but the result may be printed on a sheet or may be output by voice.

The above-described embodiment and the above-described various modifications are merely examples of the present invention, and it is a matter of course that modifications, changes, additions, and the like appropriately made within the scope of the gist of the present invention are included in the claims of the present application.

[Various Modes]

It is obvious for those skilled in the art that the above-described exemplary embodiment is a specific example of the following aspects.

(Clause 1) A document search support device according to the present invention is a device configured to support work of searching document data used for interpretation of an information analysis result of analysis data obtained by analyzing a sample containing an analyte using an analyzer, the document search support device including:

an information acquisition unit configured to acquire first information for identifying the analyte from the analysis data;

an information reception unit configured to receive input of second information for searching data of document used for interpretation of the information analysis result of the analysis data;

an extraction unit configured to extract, based on the first information and the second information, a plurality of relevant terms which are terms relevant to the information analysis result of the analysis data, from among terms included in data of documents in a database where data of documents is stored;

a score calculation unit configured to calculate, for each of the plurality of relevant terms, a relevance score indicating a degree of relevance between the relevant term and the first information, and a relevance score indicating a degree of relevance between the relevant term and the second information; and a statistical processing unit configured to obtain an index value of statistical likelihood of each of the plurality of relevant terms from the relevance scores of the relevant term.

In the document search support device of the present invention, the first information is, for example, the name of an analyte, a name representing a category of the analyte, combination of the name of the analyte and concentration, and the like. In a case where there are a plurality of analytes, the information acquisition unit acquires, as the first information, the names of the plurality of analytes, or combination of the names of the plurality of analytes and the content of each analyte contained in the sample.

The second information is, for example, information input by a person in charge of interpretation of the information analysis result of analysis data, and is information reflecting the purpose of analyzing the analyte. When the purpose of analyzing the analyte is to elucidate the action mechanism of a drug, the name of the disease of the patient to whom the drug is administered, the name of the medicinal properties contained in the drug, the name of the tissue on which the medicinal properties acts, and the like are input as the second information by the interpreter, and received by the information reception unit.

The "index value of statistical likelihood" of a relevant term in the present invention is a value representing the probability that the relevant term has been extracted (not) by chance.

According to the document search support device of Clause 1, since the index value of statistical likelihood is obtained for each of the plurality of relevant terms extracted by the extraction unit, it is possible to determine which relevant term is effective for search of literatures necessary for interpretation of the information analysis result of analysis data from the index value of each relevant term, and it is possible to efficiently extract document data useful for interpretation of the information analysis result of analysis data by using the relevant term.

(Clause 2) In the document search support device of Clause 1, the statistical processing unit can be configured to obtain a p value of a relevance score of each relevant term as the index value.

(Clause 3) In the document search support device of Clause 1, the statistical processing unit can be configured to obtain the index value of each relevant term using multiple comparison correction.

(Clause 4) In the document search support device of Clause 1, the statistical processing unit can be configured to obtain FDR of a relevance score of each relevant term as the index value.

According to the document search support device of Clause 2 to Clause 4, it is possible to perform a statistical hypothesis test, and to find whether a relevance score is statistically significant.

(Clause 5) The document search support device of Clause 1 can include a display control unit configured to cause a display unit to display the plurality of relevant terms in descending order or ascending order of the index value.

According to the document search support device of Clause 5, it is found as to which relevant term among the plurality of relevant terms displayed on the display unit to preferentially use to search document data.

(Clause 6) The document search support device of any of Clause 1 to Clause 5 can include:
a determination unit configured to determine whether or not the index value is within a predetermined normal range; and
a display control unit configured to cause a display unit to display a relevant term of which the index value is not within the normal range and a relevant term of which the index value is within the normal range in a distinguished manner.

(Clause 7) The document search support device of any of Clause 1 to Clause 5 can include:
a determination unit configured to determine whether or not the index value is within a predetermined normal range; and
a display control unit configured to cause a display unit to display only a relevant term of which the index value is within the normal range.

According to the document search support device of Clause 6 and Clause 7, it is possible to easily recognize a relevant term useful for search of document data.

(Clause 8) In the document search support device of Clause 1, document data stored in the database includes information for identifying a literature and a search term for searching for the literature associated with the information that are set for each of a plurality of literatures, and
the statistical processing unit can be configured to perform enrichment analysis by classifying, by category, a plurality of relevant terms extracted by the extraction unit, and obtain a category in which the number of extracted relevant terms is statistically significantly large.

According to the document search support device of Clause 8, a category in which the number of extracted relevant terms is judged to be statistically significantly large can be a trigger for considering a sample analysis method or reviewing the second information. That is, in a case where the purpose of analyzing the sample and the category deviate from each other, it can be estimated that there is a possibility that the analysis method of the sample is wrong or the term input as the second information is not appropriate.

(Clause 9) In the document search support device of Clause 8, the statistical processing unit can be configured to perform cross tabulation of a plurality of relevant terms by category and obtain a category in which the number of relevant terms is statistically significantly large by chi-square analysis.

(Clause 10) In the document search support device of Clause 8, the statistical processing unit can be configured to perform cross tabulation on a plurality of relevant terms by category and obtain a category in which the number of relevant terms is statistically significantly large by chi-square analysis and residual analysis.

(Clause 11) In the document search support device according to Clause 9 or Clause 10, the statistical processing unit can be configured to perform multiple test correction on a result of performing cross tabulation on a plurality of relevant terms by category.

According to the document search support device of Clause 9 to Clause 11, it is possible to find as to which category a large number of relevant terms of a plurality of extracted relevant terms have been extracted. For example, in a case where a result that there are significantly many categories relevant to a certain phenomenon or a certain mechanism is obtained, the analyzer or analyst can notice that the phenomenon or the mechanism can be relevant to his/her research.

(Clause 12) The document search support device according to any of Clause 8 to Clause 11 can include a display control unit configured to cause a display unit to display a relevant term belonging to a category in which the number of relevant terms is statistically significantly large in a distinguished manner from other relevant terms.

According to the document search support device of Clause 12, it is possible to easily recognize a category including many relevant terms useful for search of document data.

REFERENCE SIGNS LIST

10 . . . Mass Spectrometer
11 . . . Device Main Body
12 . . . Personal Computer
20 . . . Internet
21 . . . Tablet Terminal
21 . . . Terminal Device
22 . . . Personal Computer
41, 42, 43, 44 . . . Database
50 . . . Document Search Support Device
51 . . . Control Unit
511 . . . Analysis Processing Unit
512 . . . Information Acquisition Unit
513 . . . Information Reception Unit
514 . . . Extraction Unit
515 . . . Statistical Processing Unit
516 . . . Display Control Unit
52 . . . Arithmetic Operation Device
53 . . . Auxiliary Storage Device
54 . . . Communication Unit
57 . . . Display Control Unit
58 . . . Input Unit
59 . . . Display Unit
60 . . . Device Main Body

The invention claimed is:

1. A document search support device configured to support work of searching document data used for interpretation of an information analysis result of analysis data obtained by analyzing a sample containing an analyte using an analyzer, the document search support device comprising:
an information acquisition unit configured to acquire first information for identifying the analyte from the analysis data;
an information reception unit configured to receive input of second information for searching data of a document used for interpretation of an information analysis result of the analysis data;
an extraction unit configured to extract, based on the first information and the second information, a plurality of relevant terms that are terms relevant to the information analysis result of the analysis data, from among terms included in the data of documents in a database where data of documents is stored;

a score calculation unit configured to calculate, for each of the plurality of relevant terms, a relevance score indicating a degree of relevance between the relevant term and the first information, and a relevance score indicating a degree of relevance between the relevant term and the second information; and a statistical processing unit configured to obtain an index value of statistical likelihood of each of the plurality of relevant terms from the relevance scores of the relevant term.

2. The document search support device according to claim 1, wherein the statistical processing unit is configured to obtain a p value of a relevance score of each relevant term as the index value.

3. The document search support device according to claim 1, wherein the statistical processing unit is configured to obtain the index value of each relevant term using multiple comparison correction.

4. The document search support device according to claim 1, wherein the statistical processing unit is configured to obtain FDR of a relevance score of each relevant term as the index value.

5. The document search support device according to claim 1 comprising a display control unit configured to cause a display unit to display the plurality of relevant terms in descending order or ascending order of the index value.

6. The document search support device according to claim 1 comprising:
a determination unit configured to determine whether or not the index value is within a predetermined normal range; and
a display control unit configured to cause a display unit to display a relevant term of which the index value is not within the normal range and a relevant term of which the index value is within the normal range in a distinguished manner.

7. The document search support device according to claim 1 comprising:
a determination unit configured to determine whether or not the index value is within a predetermined normal range; and
a display control unit configured to cause a display unit to display only a relevant term of which the index value is within the normal range.

8. The document search support device according to claim 1, wherein
document data stored in the database includes information for identifying a literature and a search term for searching for the literature associated with the information that are set for each of a plurality of literatures, and
the statistical processing unit is configured to perform enrichment analysis by classifying, by category, a plurality of relevant terms extracted by the extraction unit, and obtain a category in which the number of extracted relevant terms is statistically significantly large.

9. The document search support device according to claim 8, wherein the statistical processing unit is configured to perform cross tabulation of a plurality of relevant terms by category and obtain a category in which a number of relevant terms is statistically significantly large by chi-square analysis.

10. The document search support device according to claim 8, wherein the statistical processing unit is configured to perform cross tabulation of a plurality of relevant terms by category and obtain a category in which a number of relevant terms is statistically significantly large by chi-square analysis and residual analysis.

11. The document search support device according to claim 9, wherein the statistical processing unit is configured to perform multiple test correction on a result of performing cross tabulation on a plurality of relevant terms by category.

12. The document search support device according to claim 8 comprising a display control unit configured to cause a display unit to display a relevant term belonging to a category in which a number of relevant terms is statistically significantly large in a distinguished manner from other relevant terms.

13. A document search support method for supporting work of searching document data used for interpretation of an information analysis result of analysis data obtained by analyzing a sample containing an analyte using an analyzer, the document search support method comprising:
acquiring first information for identifying the analyte from the analysis data;
receiving input of second information for searching data of a document used for interpretation of an information analysis result of the analysis data;
extracting, based on the first information and the second information, a plurality of relevant terms which are terms relevant to an information analysis result of the analysis data, from among terms included in data of documents in a database where data of documents is stored;
calculating, for each of the plurality of relevant terms, a relevance score indicating a degree of relevance between the relevant term and the first information, and a relevance score indicating a degree of relevance between the relevant term and the second information; and
obtaining an index value of statistical likelihood of each of the plurality of relevant terms from the relevance scores of the relevant term.

* * * * *